US011109952B2

(12) United States Patent
Andersson et al.

(10) Patent No.: US 11,109,952 B2
(45) Date of Patent: Sep. 7, 2021

(54) VAGINAL DEVICE

(71) Applicant: Invent Medic Sweden AB, Lund (SE)

(72) Inventors: Ulrika Andersson, Höganäs (SE);
Elisabeth Sthengel, Helsingborg (SE);
Karin Bryder, Gothenburg (SE); Line Irene Andersen, Oslo (NO)

(73) Assignee: Invent Medic Sweden AB, Lund (SE)

( * ) Notice: Subject to any disclaimer, the term of this patent is extended or adjusted under 35 U.S.C. 154(b) by 0 days.

(21) Appl. No.: 17/046,706

(22) PCT Filed: Apr. 11, 2019

(86) PCT No.: PCT/EP2019/059357
§ 371 (c)(1),
(2) Date: Oct. 9, 2020

(87) PCT Pub. No.: WO2019/197585
PCT Pub. Date: Oct. 17, 2019

(65) Prior Publication Data
US 2021/0113318 A1    Apr. 22, 2021

(30) Foreign Application Priority Data

Apr. 11, 2018  (SE) .................................... 1850402-7

(51) Int. Cl.
*A61F 2/00*   (2006.01)
(52) U.S. Cl.
CPC ...... *A61F 2/005* (2013.01); *A61F 2230/0008* (2013.01); *A61F 2230/0013* (2013.01);
(Continued)
(58) Field of Classification Search
CPC .... A61F 2/0004; A61F 2/0009; A61F 2/0031; A61F 2/005
See application file for complete search history.

(56) References Cited

U.S. PATENT DOCUMENTS

| 6,110,099 A | 8/2000 | Benderev |
| 2009/0203959 A1* | 8/2009 | Ziv .......................... A61F 2/005 600/29 |

(Continued)

FOREIGN PATENT DOCUMENTS

| CA | 2691663 | 8/2011 |
| WO | WO 00/67662 | * 11/2000 ............... A61F 2/00 |

OTHER PUBLICATIONS

Written Opinion and International Search Report for Application No. PCT/EP2019/059357 dated Jul. 23, 2019; 14 pages.

*Primary Examiner* — Suba Ganesan
(74) *Attorney, Agent, or Firm* — Knobbe, Martens, Olson & Bear, LLP

(57) ABSTRACT

A vaginal device and method of preventing urinary incontinence is disclosed. The device includes a longitudinal portion having a geometrical centre line, a first end and a second end, the first end being the innermost of the vaginal device during use, at least one supporting portion protruding from the longitudinal portion at the first end, the at least one supporting portion being configured to support against the urethra, through the vaginal wall, at a site located adjacent the maximal urethral pressure point, and a reference member protruding from the longitudinal portion at the second end, wherein the reference member during use is fixated against the vaginal introitus, holding the vaginal device securely fixated inside of the vagina and ensuring the at least one supporting portion is arranged at the intended site. The device further includes a section of the longitudinal portion, arranged between the supporting portion and the reference member, that has a decreasing cross-section towards the reference member and/or has at least one notch, groove and/or slot in an outer surface along an axial direction of the section.

11 Claims, 3 Drawing Sheets

(52) U.S. Cl.
CPC ............... *A61F 2230/0023* (2013.01); *A61F 2230/0054* (2013.01); *A61F 2250/0039* (2013.01)

(56) References Cited

U.S. PATENT DOCUMENTS

2011/0295058 A1* 12/2011 Henriksson .......... A61N 1/0524
600/37
2017/0071715 A1   3/2017  Hendriksson et al.
2018/0021120 A1   1/2018  Kanner et al.

* cited by examiner

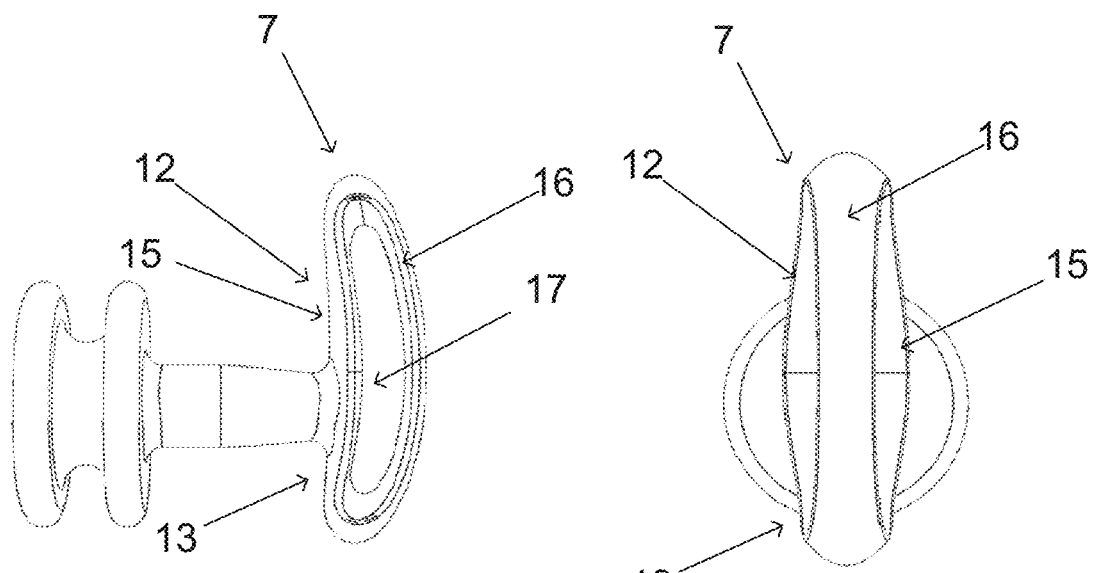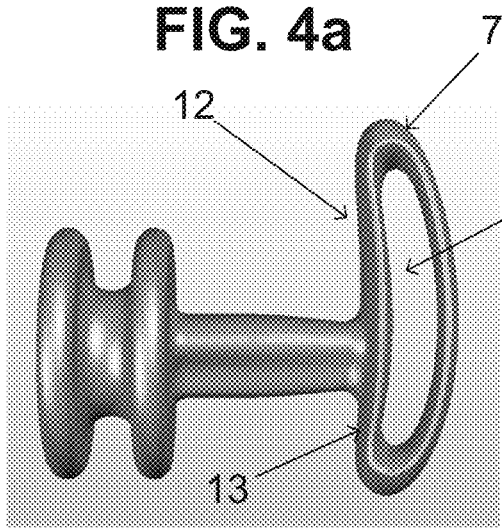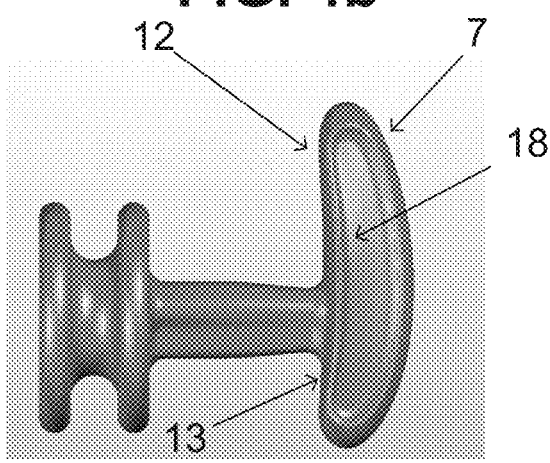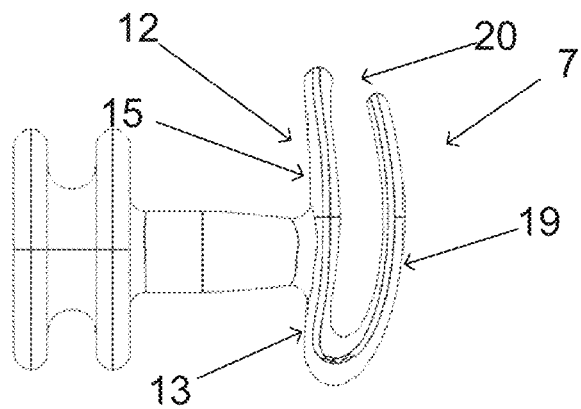

VAGINAL DEVICE

BACKGROUND OF THE INVENTION

Field of the Invention

The present invention relates to a vaginal device intended as an aid for women suffering from urinary stress incontinence.

Background of the Invention

Urinary incontinence is a public health issue which affects more than 13 million women in the USA only. There exist different types of urinary incontinence in women, such as urge incontinence, stress incontinence and mixed incontinence. Women having urge incontinence suffer from at least some unwanted leakage caused by urgency. The focus herein is urinary stress incontinence; however, the device is also likely to relieve urge incontinence. Of the number of women suffering from urinary incontinence about half of them suffer from stress incontinence. Urinary stress incontinence is mainly caused by connective tissue laxity or damage in the vagina or its supporting ligaments. The background to urinary stress incontinence and its origin may be described by the Integral Theory (An integral theory and its method for the diagnosis and management of female urinary incontinence, Petros P E, Ulmsten Ul, Scand J Urol Nephrol Suppl, 1993; 153:1-93), which states that connective tissue damage to the 3 zones of the Integral System, which encompasses all three pelvic organs, bladder, vagina and anorectum, is the ultimate cause of prolapse and dysfunction in these organs. In other words, stress incontinence may be caused by a defect function of the tissue and/or ligaments connecting the urethra and vaginal wall with the pelvic muscles and pubic bone. Women having had vaginal delivery, have chronic cough, suffering from obesity or traumas to the pelvic floor are more proned for stress incontinence. However, genetic factors may also be of importance and may cause these defect functions.

Today there exist surgical methods supported by the knowledge of the Integral Theory. For example, U.S. Pat. No. 5,899,909 discloses a surgical method for restoration of incontinence, the today called TVT (tension free vaginal tape) method which is a method effectively preventing and eliminating stress incontinence. U.S. Pat. No. 5,899,909 discloses a method comprising the steps of passing a tape into the body via the vagina first at one end thereof and then at the other end thereof at one side and the other, respectively, of urethra to form a loop around urethra, located between urethra and the upper vaginal wall, extending said tape over the pubic bone and through the abdominal wall, the ends of the tape being available outside the abdominal wall, tightening said strap at said ends, and leaving the tape implanted in the body. The tape is left permanently in the body to provide itself, as an artificial ligament, the reinforcement of the tissue required in order to restore the urinary incontinence, and/or to provide said reinforcement by the development of fibrous tissue.

The method disclosed according to U.S. Pat. No. 5,899,909 works very well. However, it is a surgical method and as such it is not available for all women in need of help to reduce or eliminate stress incontinence problems. Since stress incontinence in women is an extensive, widely spread problem all around the world, it is firstly not possible to treat everyone in need of a surgical treatment and secondly, in several countries, the possibility of receiving a TVT surgery is very limited. Moreover, many women sufferings from stress incontinence prefer conservative treatment or are not suitable for TVT surgery, for instance due to high age or wanting to give birth. Furthermore, in countries not having free medical service, or with only parts of that service being free, there will be many women having this problem but not the financial means to pay for a TVT surgery.

There exist today different devices with the purpose of alleviating incontinence in women. U.S. Pat. No. 6,739,340 discloses a device for prevention of involuntary urination. The device comprises a body for arrangement in the vagina for compressive action on and support of the neck of the bladder and optionally the urethra. The body has a substantially elongated shape with a longitudinal axis extending, in the intended direction of insertion, from a proximal to a distal end and is made from a compressive and elastically deformable material. The body comprises at least one part which is protruding from the outer surface of the body which is said to provide at least one pressure area for contact with the neck of the bladder and optionally the urethra.

U.S. Pat. No. 6,645,137 discloses a vaginal insert having a flexible body either in the form of a belt or a split cylinder. In either case, the insert may be into a coiled state. The body is said to have a reduced diameter when coiled and exhibits a resilient bias toward uncoiling and expanding in diameter from the coiled state by being restricted by an applicator tube. When the insert is inserted into the vagina of a patient, it is said to expand and press against the vaginal wall, such as for treating incontinence. A medicament may be combined with the insert that is introduced to the patient through contact with the insert, such as for treating incontinence with a drug as well as pressure. The belt-type body may incorporate mating ridges and grooves to keep the insert in a cylindrical shape. Latch elements may be incorporated on the insert to support the insert in an expanded, partially uncoiled state. There are disadvantages with the known vaginal devices disclosed above. Firstly, none of these devices are securely fixated inside of the vagina during normal use. When women move or for instance exercise there exists a great risk for movement of these devices inside the vagina. Another circumstance when this problem may be extensive is during a sneeze when the pressure power inside of the vagina is very large. This may also render the vaginal devices being pushed down towards the opening of the vagina. These cases of movement of the vaginal devices inside of the vagina render the pressing elements, that is the at least one protruding part in U.S. Pat. No. 6,739,340 and the protruding coils in U.S. Pat. No. 6,645,137, of the vaginal devices to press on the wrong site of the vaginal wall or urethra. In those cases these vaginal devices have only limited effect or no effect at all with respect to the prevention of stress incontinence. Moreover, both devices may be harmful for the patient or be perceived as unpleasant to use. This is caused by the designs of the pressing elements of these vaginal devices.

WO2010074635 discloses a vaginal device for the prevention of incontinence of the type called urinary stress incontinence, which vaginal device may function as an alternative for a patient not suitable for or one does not want to undergo a TVT surgery and which vaginal device solves the problems described above with up to now known vaginal devices.

An object of the present invention is to provide an improved vaginal device which is more comfortable for the user and easier to handle.

SUMMARY OF THE DISCLOSURE

The object above is solved by a vaginal device of an elastic material, and wherein a portion of a longitudinal portion, between a supporting portion and a reference member has a decreasing cross-section towards the reference member. In some examples the portion has at least one notch, groove or slot in an outer surface along an axial direction.

In a first aspect of the disclosure, a vaginal device for preventing urinary incontinence made of an elastic material is described. The vaginal device may comprise a longitudinal portion having a geometrical centre line, a first end and a second end, the first end being the innermost of the vaginal device during use. The device may further include at least one supporting portion protruding from the longitudinal portion at the first end, the at least one supporting portion may be configured to support against the urethra, through the vaginal wall, at a site located adjacent the maximal urethral pressure point. The device further may include a reference member protruding from the longitudinal portion at the second end, wherein the reference member during use may be fixated against the vaginal introitus, holding the vaginal device securely fixated inside of the vagina and ensuring the at least one supporting portion may be arranged at the intended site. A section of the longitudinal portion, arranged between the at least one supporting portion and the reference member, may have a decreasing cross-section towards the reference member and/or the section may have at least one notch, groove and/or slot in an outer surface along an axial direction of the section.

In one example, the section of the longitudinal portion of the vaginal device may have a single notch, groove or slot. The single notch, groove and/or slot provides the cross-section of the portion with a U-shape and/or V-shape.

In one example, the section of the longitudinal portion of the vaginal device may have two notches, grooves and/or slots connected by two arches, such as two arched surfaces. The arched surfaces have the shape of extrados surfaces, i.e. an outer curve of an arch. The shape of the surfaces connecting the two notches, grooves and/or slots may also be described as two curved surfaces radially protruding from a centre line, such as two bulging surfaces or as surfaces having an arced shaped.

Alternatively, the shape of the section of the longitudinal portion may be defined as at least sections of at least two longitudinally joined cylinders, where the notches, grooves and/or slots are obtained between the longitudinally joined sections of the cylinders. The diameters of the longitudinally joined cylinders may be the same, or they may be different.

In one example may one of the two arches be longer than the other, whereby a cross-section of the section of the longitudinal portion resembles a key-hole shape.

In one example may the reference member be protruding at an angle from the longitudinal portion in a first direction towards the anus, when in use, and/or a second direction towards the clitoris, when in use. For example, a first section of the reference member may be configured to be protrude towards the anus, when in use and/or a second member of the reference member may be configured to protrude towards the clitoris, when in use.

In one example may a first section of the reference member protrudes longer in a first direction towards the anus than a second direction towards the clitoris.

In one example may the reference member have a curved top section and a bottom section. The bottom section may have a flat shape. The curved top section may be connected to the bottom section, at least to a first end of the bottom section which may protrude towards the anus, when in use, or to a second end of the bottom section which may protrude towards the clitoris, when in use. For example, the curved top section may be connected to an end of the first section configured to protrude towards the anus, and/or to an end of the second section configured to protrude towards the clitoris.

In one example may the reference member be widest at a connection point with the second end of the longitudinal portion.

In one example may the reference member be wider than the cross-section of the second end of the longitudinal portion at the connection point.

In another aspect of the disclosure is a method of preventing urinary incontinence described. The method may comprise supporting the urethra, through the vaginal wall, at a site located adjacent the maximal urethral pressure point, by arranging at least one supporting portion protruding from a longitudinal portion having a geometrical centre line, a first end and a second end, the first end being the innermost of the vaginal device during use. The method may further include fixating the supporting portion at its intended site by arranging a reference member protruding from the longitudinal portion at the second end against the vaginal introitus, holding the vaginal device securely fixated inside of the vagina. The method may also include providing lower weight with maintained stability by including a section of the longitudinal portion arranged between the at least one supporting portion and the reference member, having a decreasing cross-section towards the reference member and/or having at least one notch, groove and/or slot in an outer surface along an axial direction of the section.

In some examples may the intended site be located between close to the maximal urethral pressure point and the bladder neck.

As is mentioned above, during use, said at least one supporting portion of the vaginal device according to the present disclosure is intended to support against the urethra, through the vaginal wall, for example at a site located between close to the maximal urethral pressure point and the bladder neck. The maximal urethral pressure point of the urethra is situated close to the middle point of the urethra or the mid urethra as it is also called. When a woman is about to sneeze or cough, the pressure built up along the urethra is the highest at this maximal urethral pressure point where the muscular pressure gets additional forces from the bending of the proximal portion of urethra in downward direction at the "urethral knee". The fixation of the distal portion of a normal urethra at the "urethral knee" is due to the support from the posterior urethral ligaments on both sides of the urethra which connect the symphysis pubis with the urethra and the anterior vaginal wall. Due to compression of the urethra and a "curtsy effect" of the "urethral knee" during a pressure built up due to e.g. sneezing or coughing, this area is important to support so that the depression of the "urethral knee" decreases. This is accomplished by the at least one supporting portion of the vaginal device according to the present disclosure. Preferably, the at least one supporting portion according to the present disclosure supports against the urethra, through the vaginal wall, for example against the maximal urethral pressure point or very close to it. At this site, the maximal effect is obtained. According to the present disclosure, however, the at least one supporting portion may also support at sites between close to the maximal urethral pressure point and the bladder neck, such as at several sites. Moreover, the expression "close to the maximal urethral pressure point" should in this case be interpreted as possible sites on both sides of the maximal urethral pressure point, and not only on that side facing towards the bladder neck. The supporting portion of the vaginal device according to the present invention will support the lax urethra, through the vaginal wall, in cases of stress incontinence caused by laxity of the posterior urethral ligaments. In rest there will be no or very little compression of the urethra, which can interfere with the blood circulation. This is also important due to the fact that the vaginal device according to the present invention should be comfortable to use. This is also a difference in comparison to vaginal devices according to state of the art which are stated to press against the urethra through the vaginal wall. Furthermore, the at least one supporting portion according to the present disclosure must be designed to be able to support the urethra at times when the pressure built up is very high, such as when a woman is about to sneeze. This supporting feature of the vaginal device according to the present disclosure requires that the at least one supporting portion is flexible in its nature, both in terms of material and construction, but also able to support the urethra at the intended site when the pressure wave along the urethra is large. Another very important difference of the vaginal device according to the present disclosure in comparison to known devices is the reference member of the present invention. The reference member protrudes from the longitudinal portion at the lower end and is fixated against the vaginal introitus. The reference member fixates the vaginal device in place so that the at least one supporting portion supports the urethra at the intended site. This reference member is of great importance. When women are moving there is an evident risk for vaginal devices to slide out of place inside of the vagina. In such a case, when and if a pressure wave arises from the abdomen, such as when sneezing or coughing, the vaginal device will not be fixated at the right place. This problem is solved by the vaginal device according to the present disclosure, having the reference member making sure that the vaginal device and hence at least one supporting portion to be fixated to support the urethra, through the vaginal wall, at the intended site.

Moreover, the fixation of the reference member against the vaginal introitus is also of importance. The tissue against and around the vaginal introitus (labium minorae and majorae) shall be able to close around the reference member, so that the reference member and vaginal device are fixated securely. This means that the fixation is made so that the reference member is positioned at the labia minora, against the vaginal introitus, and not the labia majora. Due to the fact that labia majora comprises fatty tissue and the size of the labia majora differs a lot from woman to woman, it is difficult to design a reference member for fixation outside the labia majora.

The vaginal device according to the present disclosure may have different design. For example, the at least one supporting portion does not have to protrude around the longitudinal portion. It is, however, important that the at least one supporting portion of the vaginal device protrudes in the intended direction towards the urethra during use. As long as the at least one supporting portion is possible to support against the urethra, through the vaginal wall, the design thereof may vary. If the longitudinal portion has a larger diameter it is possible to design the vaginal device so that the longitudinal portion in fact supports against the vaginal wall. In such a case, the at least one supporting portion shall not protrude in all directions from the longitudinal portion, that is, shall not protrude around the longitudinal portion, due to the fact that the vaginal device as a whole in that case would not be able to be inserted in the vagina, or at least would not be comfortable to use. In such a case, the at least one supporting portion may e.g. have a half-moon shape or the like so that the supporting portion only protrudes in an intended direction against the urethra. Many other shapes of the at least one supporting portion are also possible, such as flower-shaped and protruding around the longitudinal portion, protruding around the longitudinal portion asymmetrically, but of course also a circular shaped disc which hence protrudes symmetrically around the longitudinal portion. In the latter case, the diameter of the longitudinal portion of course is smaller in comparison with the case of a half-moon shaped supporting portion due to the fact that the at least one supporting portion protrudes around the longitudinal portion and as such bears against the vaginal wall in all directions.

BRIEF DESCRIPTION OF THE DRAWINGS

These and other aspects, features and advantages of which examples of the disclosure are capable of will be apparent and elucidated from the following description of embodiments of the present disclosure, reference being made to the accompanying drawings, in which:

FIGS. 4a to 4e are illustrating examples of the vaginal devices according to the current disclosure.

DETAILED DESCRIPTION OF THE DISCLOSURE

Figure 1:
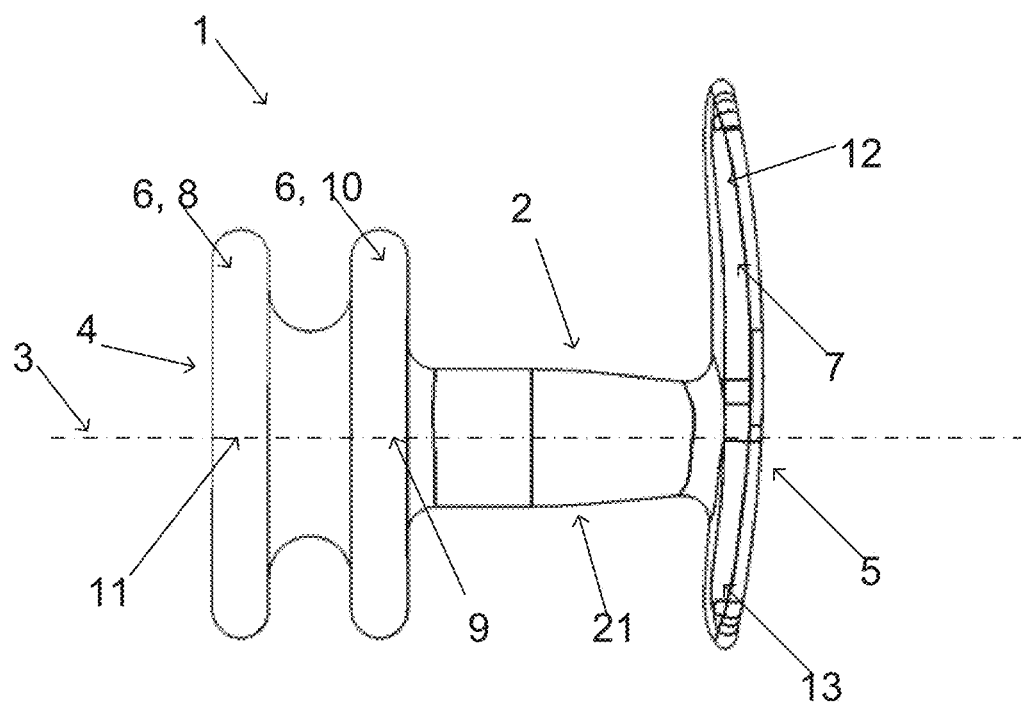
FIG. 1 is illustrating a side view of a vaginal device according to the present disclosure.

Specific examples of the disclosure will be described with reference to the accompanying drawings. This disclosure may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the disclosure. In the drawings, like numbers refer to like elements.

The following description focuses on examples of the present disclosure applicable to a vaginal device for preventing urge incontinence, stress incontinence and mixed incontinence. However, it will be appreciated that the disclosure is not limited to this application but may be applied to many other types of symptoms which may be improved by support of the urethra through the vaginal wall. As is mentioned above, the vaginal device according to the present disclosure is made of an elastic material. The degree of hardness of materials possible to use for the vaginal device may be measured by shore A. Examples of possible materials may e.g. have a shore A of 10-50, e.g. 10-40, 10-30, 20-40 or 20-30. According to another example of the present disclosure, the vaginal device is made of an elastic material of medical quality, that is an inert material. Furthermore, the material may be roentgen visualised. The latter may be of interest so that the vaginal device is visible for X-ray examination so that it is possible to see where the vaginal device according to the present invention supports the urethra, through the vaginal wall. Examples of possible elastic materials, that is elastic tissue accepted inert materials, are polyurethane, silicone rubber, latex rubber, polystyrene copolymer materials and natural rubber, or combinations thereof. Other elastic tissue accepted inert materials are of course also possible to use.

As is mentioned above, the design of the supporting portion according to the present disclosure may vary, but the important characteristic of the portion is the supporting feature. According to one example, the at least one supporting portion is resilient in a radial direction towards the urethra through the vaginal wall. This implies that the supporting portion during support of the urethra, through the vaginal wall, may fold itself somewhat in a radial direction, that is fold longitudinal to the longitudinal portion. This may be of interest due to the fact that this may give an optimized support to the urethra without pressing too hard on the vaginal wall, and consequently the vaginal wall may not be damaged by ischaemia. Moreover, it may also give an increased comfort for the user in comparison to the known vaginal devices. The possible radial resilience towards the urethra through the vaginal wall according to the present disclosure may also be something that differs from the known vaginal devices, which only may give resilience in an axial direction towards the urethra through the vaginal wall. This may be observed by looking at the drawings of U.S. Pat. No. 6,739,340, showing at least one rigid pressing member of the device, which pressing member only is resilient due to use of a flexible material, as well as U.S. Pat. No. 6,645,137, which discloses pressing rigid rings of a similar type as is disclosed according to U.S. Pat. No. 6,739,340.

The at least one supporting portion according to the present disclosure may, however, also be of a more rigid type, such as the ones disclosed according to U.S. Pat. Nos. 6,739,340 and 6,645,137. The choice of the elastic material and the hardness thereof of the vaginal device are important in this sense. A thick at least one supporting portion is e.g. possible according to the present invention if a soft elastic material having a low hardness (shore A) is chosen for the vaginal device. This gives a supporting portion which is not resilient in a radial direction towards the urethra through the vaginal wall, but due to the choice of a soft elastic material, the supporting portion may give both enough support to the urethra, through the vaginal wall, and still be harmless to the vaginal wall and comfortable to use. The choice of the design of the at least one supporting portion according to the present disclosure depends in other words on several parameters, such as if only one supporting portion is intended, the material of the vaginal device and hence supporting portion or portions and the thickness and material thereof. As mentioned above, the design of the at least one supporting portion may vary. According to one example of the present disclosure, the at least one supporting portion protrudes all around the longitudinal portion. This implies that the at least one supporting portion or supporting member e.g. may look like flower-shaped or like a circular disc if the vaginal device is viewed from above. According to another example of the disclosure, the at least one supporting portion protrudes all around the longitudinal portion and is substantially circular in a plane perpendicular to the geometrical centre line. This implies a disc-like supporting portion disclosed above. Moreover, the vaginal device according to the present disclosure may be provided with some specific features. According to one example, the vaginal device of the present disclosure comprises at least one perforation going through the at least one supporting portion. This at least one perforation may be provided to avoid a feel of suction/vacuum upon removal of the device.

The size of the different parts of the vaginal device may vary. For example, the diameter of the vaginal device, especially at its widest place, may vary. This is due to the fact that the size of vaginas of women may vary. Therefore, according to one example, the at least one supporting portion protrudes all around the longitudinal portion, is substantially circular in a plane perpendicular to the geometrical centre line and has a diameter of 25-45 mm, such as 25-40 mm, 25-35 mm, 30-45 mm, 30-35 mm, 35-45 mm, 35-40 mm, 40-45 mm. Examples of some possible diameters are 30, 35 and 40 mm. Although this example discloses at least one supporting portion or supporting member being substantially circular, other shapes are possible as well, such as the flower-shaped supporting portion mentioned above. In such a case, the diameter should be interpreted as the length from a most protruding point of the supporting portion on one side of the longitudinal portion to another most protruding point of the supporting portion on the other side of the longitudinal portion, through a geometrical centre inside of the longitudinal portion.

As said above, the diameter of the longitudinal portion may vary, dependent inter alia on if the supporting portion is protruding all around the longitudinal portion. According to one example of the present disclosure, the longitudinal portion is circular and has a diameter of 10-20 mm, such as 10-15 mm, 15-20 mm, e.g. 15 mm. A substantially circular cross section of the longitudinal portion is advantageous due to the fact of a better fit inside of the vagina.

The length of the vaginal device may also vary. However, there exists a lower possible threshold due to the fact that the vaginal device should make it possible for the supporting portion to support at the possible intended sites of the urethra. An upper limit exists also due to obvious reasons. This upper limit is about 90 mm since the normal length of the vagina up to the anterior fornix is about that length in rest. According to one example of the present disclosure, the longitudinal portion has a length of 40-80 mm from a first end to a second end, the first end being the innermost of the vaginal device during use, such as 40-80 mm, 40-70 mm, 45-60 mm, e.g. 50 mm. According to yet another example of the present disclosure, the distance from the second end of the longitudinal portion to the centre of the first (as seen from the second end) of the at least one supporting portion, at the geometrical centre line, is 15-55 mm, such as 15-50 mm, 15-45 mm, 15-40 mm, 15-35 mm, 15-30 mm, 15-25 mm, 20-55 mm, 20-50 mm, 20-45 mm, 20-40 mm, 20-35 mm, 20-30 mm.

According to the present disclosure, there may be provided more than one supporting portion or supporting member along the longitudinal portion. Therefore, according to one example of the present disclosure, the vaginal device comprises at least two supporting portions protruding from the longitudinal portion, the at least two supporting portions protruding separately from each other along the longitudinal portion and all of the at least two supporting portions being intended to support against the urethra, through the vaginal wall, for example at sites located between close to the maximal urethral pressure point and the bladder neck.

According to one example of the present disclosure, the vaginal device comprises two supporting portions protruding from the longitudinal portion, wherein the two supporting portions protrude separately from each other along the longitudinal portion. The distance between the two supporting portions or supporting members may in this specific case vary, but as an example the distance between these two may be about 8-12 mm, such as 9-11 mm, such as about 10 mm, from a geometrical middle point of the second supporting portion to a geometrical middle point of the first supporting portion. This distance corresponds to that of the vaginal tape used in a TVT surgery, and with two supporting portions which are resilient in a radial direction towards the urethra through the vaginal wall, circularly shaped and hence protruding around the entire longitudinal portion, these may together support the urethra, through the vaginal wall, at the same site of the urethra as the TVT tape stabilises. To achieve this effect and to achieve an elevated resilient effect, it may be advantageous to provide two supporting portions, in the shape of circular discs described above, which protrude separately from each other along the longitudinal portion and which may have a thickness of about 3-5 mm, such as about 4 mm.

According to one example of the present disclosure, the vaginal device comprises two supporting portions protruding from the longitudinal portion, the at least two supporting portions protruding separately from each other along the longitudinal portion and both of the at least two supporting portions being intended to support against the urethra, through the vaginal wall, at two sites located, for example between close to the maximal urethral pressure point and the bladder neck.

The design of the reference member according to the present disclosure may also vary. According to one example, the reference member may have a first section configured to protrude towards the anus, when in use, and optionally a second section configured to protrude towards the clitoris, when in use. The first section of the reference member may protrude about 20-40 mm, such as 25-35 mm, such as about 30 mm from the geometrical centre line of the longitudinal portion at the second end, and the second section of the reference member may protrude below 25 mm, such as e.g. 10-25 mm, 10-20 mm, 15-25 mm, e.g. 15 mm, from the geometrical centre line of the longitudinal portion at the second end. The meaning of the first section of the reference member, and the second section of the reference member may be understood by viewing the accompanied drawings. The first section of the reference member is that end that will be fixated against the perineum by the user. The second section of the reference member is that end facing towards the opposite direction, that is towards the clitoris but not reaching the same. This is the reason for the different length thresholds for the protrusion of the first and second section, respectively. About 25-35 mm, such as 30 mm, has proven to be a functional length for the first section of the reference member from the centre line of the longitudinal portion so that the reference member is possible to fixate against the perineum by the user in a functional way. The second section of the reference member has as mentioned a length below 25 mm from the centre line of the longitudinal portion. This is due to that the second section of the reference member should be short enough not to irritate the clitoris of a user. However, even if a vaginal device according to the present disclosure without a second section configured to protrude toward the clitoris, when in use, of the reference member is possible, such a second section may increase the stability and hence fixation of the entire vaginal device inside of the vagina during use. Without the second section of the reference member there may be some risk for the vaginal device to sway and as such fall somewhat out of the perfect position inside of the vagina, e.g. during substantial movement. The shape of the first section and second section of the reference member may e.g. be ribbons which have widths that are smaller than the diameter of the longitudinal portion.

According to one example of the present disclosure, the reference member has a first and a second section, the first section is configured to protrude about 20-40 mm from the geometrical centre line of the longitudinal portion at the second end and the second section is configured to protrude about 10-25 mm from the geometrical centre line of the longitudinal portion at the second end. 20-40 mm, such as 25-35 mm, 25-30 mm, e.g. about 30 mm, is a length interval of the first section of the reference member which may be suitable for an elevated fixation of the reference member. Moreover, about 10-25 mm, such as 10-20 mm, 10-15 mm, 15-25 mm, 15-20 mm, e.g. about 15 mm, is a length interval of the second section of the reference member which is enough for achieving good fixation of the vaginal device inside of the vagina without any risk for any swaying during powerful movement by the user, but at the same time is short enough not to irritate the clitoris of the user. The reference member of the vaginal device according to the present disclosure functions as a means for insertion and pulling out the vaginal device. The shape of the reference member may vary, but a suitable example is as a ribbon which has the same width or a thinner width than the longitudinal portion of the vaginal device according to the present disclosure. According to one example, the reference member is concave. This means that both of the first section and the second section of the reference member may have this concave shape. The possible concave shape of the first section and possibly also the shorter second section of the reference member, means that these ends bend somewhat towards the first end of the longitudinal portion. The bending or curvature in this case may not very large. This concave shape of the reference member may increase the stability and fixation of the vaginal device during use. Detailed description of the drawings FIG. 1 illustrates one example of a vaginal device 1 according to the present disclosure. The vaginal device 1 may comprise a longitudinal portion 2 having a geometrical centre line 3, a first end 4 and a second end 5. Moreover, the vaginal device 1 may comprise at least one supporting portion 6 protruding from the longitudinal portion 2. In this case the vaginal device 1 according to the present disclosure may have two circular supporting portions 6, one second 8 having a centre 11 along the geometrical centre line 3 and one first 10 having a centre 9 along the geometrical centre line 3, the supporting portions 6 may protrude symmetrically around the longitudinal portion 2. The vaginal device 1 may also comprise a reference member 7 protruding from the longitudinal portion 2 at the second end 5. During use, the reference member 7 may fixated against the vaginal introitus, holding the vaginal device 1 securely fixated inside of a vagina and ensuring the two supporting portions 6 to support against the urethra, through the vaginal wall, at an intended site located, for example between close to the maximal urethral pressure point and the bladder neck, preferably located at the maximal urethral pressure point. In this specific case, the reference member 7 may have first section 12 configured to protrude towards the anus, when in use, and a second section 13 configured to protrude towards the clitoris, when in use. The first section 12 being intended to be fixated against the perineum by the user and if done, the second section 13 of the reference member may then end facing towards the opposite direction, that is towards the clitoris but not reaching the same.

The vaginal device 1 according to the example illustrated in FIG. 1 may have a section 21 of the longitudinal portion 2 configured to lower the weight of the product without sacrificing the stability of the vaginal device 1, thereby increase the comfort for the user. This may be provided, for example, by configuring the section 21 of the longitudinal portion 2, between the at least one supporting portion 6, such as the first supporting portion 10, and the reference member 7 to have a decreasing cross-section towards the reference member 7. In a further example, the section 21 of the longitudinal portion 2 may additionally and/or alternatively have at least one notch, groove and/or slot in an outer surface along an axial direction of the centre line 3.

Additionally, in one example of the vaginal device, the reference member or the whole device is coated with a hydrophilic lubricious coating, making the device slippery when wet and thereby reducing the friction on the labia. The friction may be almost removed. Examples of such coating materials are ISurTec® and AquaGlide®.

Figure 2A:
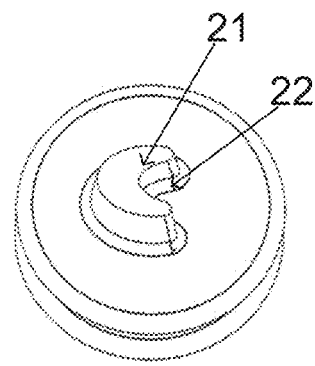
FIGS. 2a and 2b are illustrating examples of cross-sectional views of the longitudinal portions according to the disclosure.
Figure 2B:
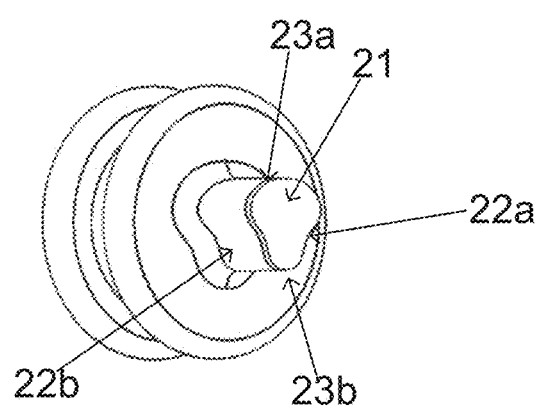

FIGS. 2a and 2b are illustrating two examples of cross-sections. FIG. 2a is illustrating an example wherein section 21 has a single notch, groove and/or slot 22, and the single notch, groove and/or slot provides a cross-section of the portion 21 with a U-shape or V-shape. In the illustrated example, may the opening of the U-shape and/or V-shape be in directed towards the clitoris, but the opposite may also be possible.

FIG. 2b is illustrating an example wherein the section 21 has two notches, grooves or slots 22a, 22b connected by two arches 23a, 23b, such as two arched surfaces. The arched surfaces 23a, 23b have the shape of extrados surfaces, i.e. an outer curve of an arch. The shape of the surfaces connecting the two notches, grooves and/or slots 22a, 22b may also be described as two curved surfaces 23a, 23b radially protruding from a centre line 3, such as two bulging surfaces or as surfaces having an arced shaped. Alternatively, the shape of the section 21 of the longitudinal portion 2 may be defined as at least sections of at least two longitudinally joined cylinders 23a, 23b, where the notches, grooves and/or slots 22a, 22b are obtained between the longitudinally joined sections of the cylinders. The diameters of the longitudinally joined cylinders may be the same, or they may be different.

Additionally, in some examples, the section 21 is solid. In some examples the longitudinal portion 2 is solid.

In the illustrated example, one of the arches 23a is longer than the other arch 23b, whereby a cross-section of the section 21 resembles a key-hole shape. In the illustrated example is the section 21 configured so that the shorted arch 23b may be arranged in a direction towards the clitoris and the longer arch 23a in a direction towards the anus. According to other examples, the opposite may also be possible.

The cross-sectional shapes illustrated in FIGS. 2a and 2b makes it possible to make the longitudinal portion 2 thinner compared to previous devices with maintained stability. Thereby provide a lower weight. It also provides the possibility of making section 21 with a cross-section which decreases towards the reference member 7. The cross-sections will also provide lower weight but also improved comfort for the user of the device.

Other cross-sectional shapes may also be viable, for example with further notches, grooves and/or slots and arches to have the cross-section of the section 21 to resemble a clover leaf, or a flower-like shape.

The width and height of the cross-section of the section 21 may be symmetric so that the width and height are the same. In some examples, the height, i.e. in a clitoris to anus direction, may be longer than the width of the cross-section. In other examples, the symmetry could have more of a triangular shape.

Figure 3A:
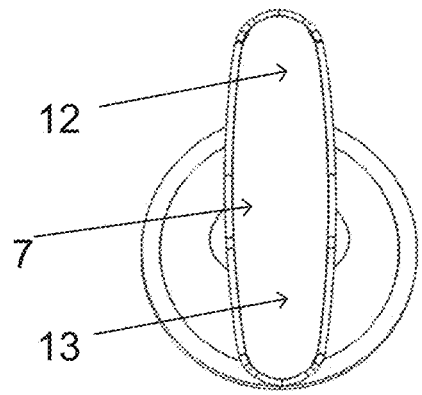
FIGS. 3a to 3c are illustrating examples of a top view, a bottom view and a cross-sectional view of a device according to the present disclosure.

FIG. 3a is illustrating the vaginal device 1 of FIG. 1 seen from the second end 5. The reference member 7 may also be the bottom section 15 of the reference members 7 illustrated in FIGS. 4a to 4e. The reference member 7 may have an oval, elliptic or oblong shape to provide good fixation against the vaginal introitus.

Figure 3B:
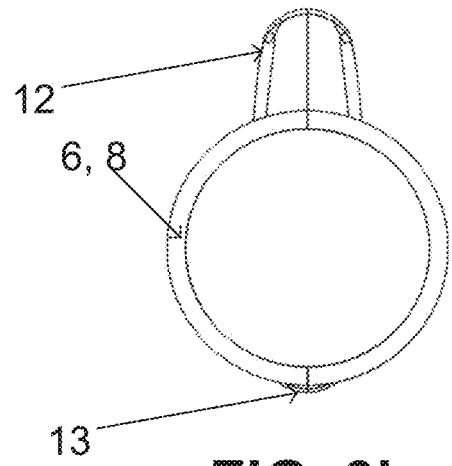

FIG. 3b is illustrating the vaginal device 1 in FIG. 1 seen from the first end 4.

Figure 3C:
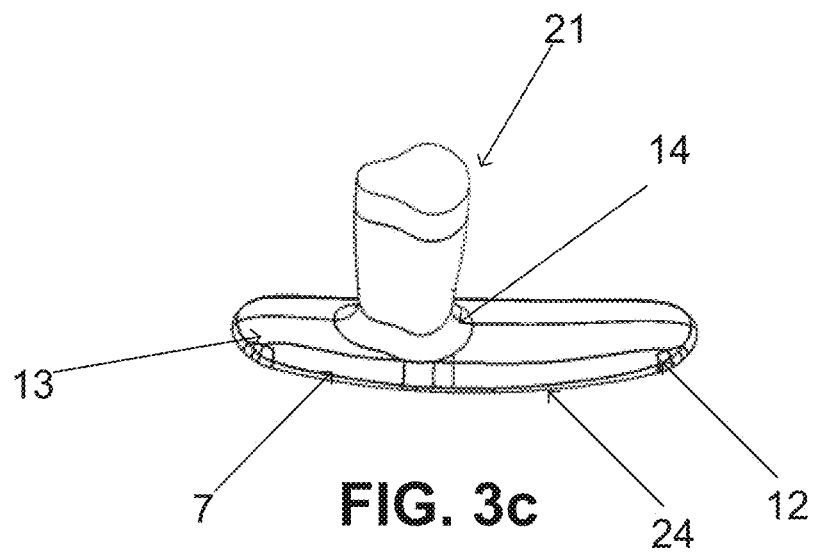

FIG. 3c is illustrating the bottom side of the reference member 7. In some example may the reference member 14 be wider than the end cross-section of the longitudinal portion 2 at a connection point 14. This may improve fixation against the vaginal introitus thereby improve stability of the vaginal device 1 when in use. In some other examples may the widest portion of the reference member 7 be at the middle of the reference member 7. Alternatively, in some other examples may the widest portion of the reference member 7 be at connection point 14, thereby providing a connection point 14 where the reference member 7 is wider than the cross-section of the end portion of the longitudinal portion 2.

As illustrated in FIG. 3c, the reference member 7 may be tapered towards an end of the first section 12 of the reference member 7 and/or an end of the second section 13 of the reference member 7. Further, the longer sides 24 of the reference member 7 may be tapered to make the edge thinner. This will improve the flexibility of the reference member and may improve the fixation against the vaginal introitus. In particular the bottom of the reference member 7 may have bevelled edges. The bevelled edges may be rounded while inclining towards the edge. A tapered or bevelled edge, especially of the longer sides 24 of the reference member 7, may improve the fixation against the vaginal introitus.

FIGS. 4a to 4e are illustrating alternative examples of the reference member 7 illustrated in FIG. 1. FIG. 4a is illustrating a reference member 7 which includes a bottom section 15, similar to the reference member 7 as illustrated in FIGS. 1, and 3a to 3c. The reference member 7 further includes a top section 16 which is curved to be connected to at least an end of the first section 12 of the bottom section 15, configured to be directed towards the anus, or an end of the second section 13 of bottom section 15, configured to be directed towards the clitoris. The bottom section 15, which may have a flat shape, and the curved top section 16 enclose an area 17. The area 17 may be hollow as illustrated in FIG. 4c. Alternatively the area may have a shallow depression 18 as illustrated in FIG. 4d.

The curved top section 16 is made to improve the handling of the vaginal device when positioning and removing the vaginal device. While a hollow area 17 allows for a light weighted vaginal device wherein the curved top section 16 is flexible and may be compressed against the bottom section 15 allowing a low profile, a depression 18 provides an improved stability of the reference member 7.

FIG. 4e is illustrating an example where the curved top section 19 is only connected or hinged to the bottom section 15 at the r end of the second section 13 and with a gap between the curved top section 19 and the bottom section 15 at the end of the first section 12. This provides further improvements on the flexibility of the curved top section 19 and also provides a lighter weight. A configuration where the curved top section 19 is only connected or hinged at one end of the bottom section 15 may also make the vaginal device easier to remove. Since the curved top section 15 may work as a string. The curved top section 19 may in some examples be connected at the end of first section 12 of the bottom section 15 which will give similar properties as when the curved top section 19 is connected to the end of the second section 13 of the bottom section 15. But the handling of the device may be slightly better when the curved top section 15 is connected to the end of the second section 13 of the bottom section 15. Especially for removal of the vaginal device.

While several examples of the present disclosure have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present disclosure. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present disclosure is/are used.

The invention claimed is:

1. A vaginal device for preventing urinary incontinence made of an elastic material, the vaginal device comprises:
   a longitudinal portion having a geometrical centre line, a first end and a second end, the first end being the innermost of the vaginal device during use;
   at least one supporting portion protruding from the longitudinal portion at the first end, the at least one supporting portion being configured to support against the urethra, through the vaginal wall, at a site located adjacent the maximal urethral pressure point;
   a reference member protruding from the longitudinal portion at the second end, wherein the reference member during use is fixated against the vaginal introitus, holding the vaginal device securely fixated inside of the vagina and ensuring the at least one supporting portion is arranged at the intended site;
   wherein a section of the longitudinal portion, arranged between the supporting portion and the reference member, has a decreasing cross-section towards the reference member and/or has at least one groove in an outer surface along an axial direction of the section.

2. The vaginal device of claim 1, wherein the section of the longitudinal portion has a single groove, and the single groove provides the cross-section of the portion with a U-shape or V-shape.

3. The vaginal device of claim 1, wherein the section of the longitudinal portion has two grooves connected by two arched surfaces.

4. The vaginal device of claim 3, wherein one of said two arched surfaces is longer than the other, whereby a cross-section of the portion resembles a key-hole shape.

5. The vaginal device of claim 1, wherein the section of the longitudinal portion has a shape defined as at least sections of at least two longitudinally joined cylinders, where at least two grooves are obtained between the longitudinally joined sections of the cylinders.

6. The vaginal device of claim 5, wherein at least one of the cylinders has a diameter different from the other.

7. The vaginal device of claim 1, wherein the reference member is protruding at an angle from the longitudinal portion in a first direction towards the anus, when in use, and/or a second direction towards the clitoris, when in use.

8. The vaginal device of claim 7, wherein the reference member protrudes longer in the first direction than the second direction.

9. The vaginal device of claim 1, wherein the reference member has a curved top section and a bottom section, and wherein the curved top section is connected to the bottom section to at least a first end of the bottom section protruding towards the anus, when in use, an/or to a second end of the bottom section protruding towards the clitoris, when in use.

10. The vaginal device of claim 1, wherein the reference member is widest at a connection point with the second end of the longitudinal portion.

11. The vaginal device of claim 10, wherein the reference member is wider than the cross-section of the second end of the longitudinal portion at the connection point.

* * * * *